United States Patent [19]

Nelson

[11] 4,073,805
[45] Feb. 14, 1978

[54] 2-DECARBOXY-2-HYDROXYMETHYL-3,7-INTER-M-PHENYLENE-11-DEOXY-PGE$_1$ COMPOUNDS

[75] Inventor: Norman A. Nelson, Galesburg, Mich.

[73] Assignee: The Upjohn Company, Kalamazoo, Mich.

[21] Appl. No.: 778,756

[22] Filed: Mar. 17, 1977

Related U.S. Application Data

[62] Division of Ser. No. 647,363, Jan. 8, 1976, Pat. No. 4,028,419.

[51] Int. Cl.$^2$ ............................................. C07C 49/82
[52] U.S. Cl. ................................................. 260/590 C
[58] Field of Search ................................... 260/590 C

[56] References Cited

U.S. PATENT DOCUMENTS 3,810,943  5/1974   Jones et al. .................... 260/590 C
3,933,892  1/1976   Chadha et al. .................. 260/468 D
3,962,312  6/1976   Hahashi et al. ................. 260/468 D

OTHER PUBLICATIONS

Pake, J. Org. Chem., vol. 34, p. 3552, (1969).

Primary Examiner—James O. Thomas, Jr.
Assistant Examiner—James H. Reamer
Attorney, Agent, or Firm—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

22 Claims, No Drawings

2-DECARBOXY-2-HYDROXYMETHYL-3,7-INTER-M-PHENYLENE-11-DEOXY-PGE₁ COMPOUNDS

The present application is a divisional application of Ser. No. 647,363, filed Jan. 8, 1976, now issued as U.S. Pat. No. 4,028,419.

The present invention relates to prostaglandin analogs for which the essential material constituting a disclosure therefor is incorporated by reference here from U.S. Pat. No. 4,028,419.

I claim:

1. A prostaglandin analog of the formula

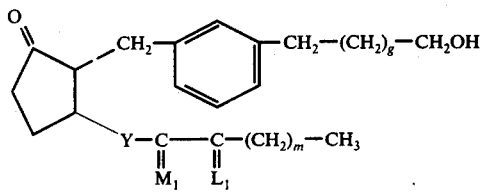

wherein Y is trans-CH=CH-;
wherein $M_1$ is

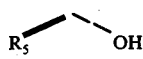

or

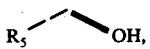

wherein $R_5$ is hydrogen or methyl;
wherein $L_1$ is

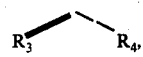

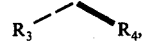

or a mixture of

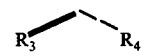

and

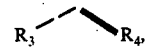

wherein $R_3$ and $R_4$ are hydrogen, methyl, or fluoro, the same or different, with the proviso that one of $R_3$ and $R_4$ is methyl only when the other is hydrogen or methyl;
wherein $g$ is 1, 2, or 3; and
wherein $m$ is 1 to 5, inclusive.

2. A compound according to claim 1, wherein $m$ is 1 or 2.

3. A compound according to claim 1, wherein $m$ is 4 or 5.

4. A compound according to claim 1, wherein $m$ is 3.

5. A compound according to claim 4, wherein $g$ is 1.

6. A compound according to claim 5, wherein at least one of $R_3$ and $R_4$ is fluoro.

7. A compound according to claim 6, wherein $R_3$ and $R_4$ are both fluoro.

8. A compound according to claim 7, wherein $R_5$ is hydrogen.

9. 2-Decarboxy-2-hydroxymethyl16,16-difluoro-3,7-inter-m-phenylene-4,5,6-trinor-11-deoxy-PGE₁, a compound according to claim 8.

10. 2-Decarboxy-2-hydroxymethyl16,16-difluoro-15-epi-3,7-inter-m-phenylene-4,5,6-trinor-11-deoxy-PGE₁, a compound according to claim 8.

11. A compound according to claim 5, wherein at least one of $R_3$ and $R_4$ is methyl.

12. A compound according to claim 11, wherein $R_3$ and $R_4$ are both methyl.

13. A compound according to claim 12, wherein $R_5$ is hydrogen.

14. 2-Decarboxy-2-hydroxymethyl16,16-dimethyl-3,7-inter-m-phenylene-4,5,6-trinor-11-deoxy-PGE₁, a compound according to claim 13.

15. 2-Decarboxy-2-hydroxymethyl16,16-dimethyl-15-epi-3,7-inter-m-phenylene-4,5,6-trinor-11-deoxy-PGE₁, a compound according to claim 13.

16. A compound according to claim 5, wherein $R_3$ and $R_4$ are both hydrogen.

17. A compound according to claim 16, wherein $R_5$ is methyl.

18. 2-Decarboxy-2-hydroxymethyl15-methyl-3,7-inter-m-phenylene-4,5,6-trinor-11-deoxy-PGE₁, a compound according to claim 17.

19. 2-Decarboxy-2-hydroxymethyl15-epi-15-methyl-3,7-inter-m-phenylene-4,5,6-trinor-11-deoxy-PGE₁, a compound according to claim 17.

20. A compound according to claim 16, wherein $R_5$ is hydrogen.

21. 2-Decarboxy-2-hydroxymethyl3,7-inter-m-phenylene-4,5,6-trinor-11-deoxy-PGE₁, a compound according to claim 20.

22. 2-Decarboxy-2-hydroxymethyl15-epi-3,7-inter-m-phenylene-4,5,6-trinor-11-deoxy-PGE₁, a compound according to claim 20.

* * * * *